United States Patent [19]

Mlinar et al.

[11] Patent Number: 4,654,309

[45] Date of Patent: Mar. 31, 1987

[54] TEST METHOD AND ARTICLE FOR ESTIMATING THE CONCENTRATION OF FREE ACID IN LIQUID

[75] Inventors: Jerry W. Mlinar, Troy Township, St. Croix County; John Neumayer, Mendota Heights, both of Minn.

[73] Assignee: Minnesota Mining and Manufacturing Co., St. Paul, Minn.

[21] Appl. No.: 721,486

[22] Filed: Apr. 9, 1985

Related U.S. Application Data

[63] Continuation-in-part of Ser. No. 554,184, Nov. 22, 1983, abandoned, which is a continuation-in-part of Ser. No. 218,356, Dec. 19, 1980, abandoned.

[51] Int. Cl.$^4$ .................... G01N 21/80; G01N 33/03
[52] U.S. Cl. .................... 436/61; 422/56; 436/20; 436/163
[58] Field of Search .................... 436/60, 61, 163, 20, 436/129, 169, 100, 166; 422/56, 57; 116/206

[56] References Cited

U.S. PATENT DOCUMENTS

| | | |
|---|---|---|
| 2,770,530 | 11/1956 | Bergstrom et al. . |
| 2,915,373 | 12/1959 | Wenker . |
| 2,953,439 | 9/1960 | Elliott et al. . |
| 3,006,735 | 10/1961 | Jordan .................... 422/56 X |
| 3,016,292 | 1/1962 | Bauer et al. . |
| 3,030,190 | 4/1962 | Seemann et al. . |
| 3,067,015 | 12/1962 | Lawdermilt .................... 116/206 X |
| 3,122,420 | 2/1964 | Rebar, Jr. et al. .................... 422/56 |
| 3,193,356 | 7/1965 | Smith .................... 436/61 |
| 3,238,020 | 3/1966 | Eiseman . |
| 3,259,463 | 7/1966 | Feasley et al. . |
| 3,420,635 | 1/1969 | Davis . |
| 3,543,570 | 12/1970 | Fijalkowski . |
| 3,552,929 | 1/1971 | Fields et al. . |
| 3,580,704 | 5/1971 | Pickup et al. .................... 436/60 |
| 3,615,226 | 10/1971 | Apter . |
| 3,682,597 | 8/1972 | Husch .................... 436/60 X |
| 3,791,988 | 2/1974 | Josef et al. . |
| 3,808,149 | 4/1974 | Ellis et al. . |
| 3,980,437 | 9/1976 | Kishimoto et al. .................... 422/56 X |
| 4,013,416 | 3/1977 | Rittersdorf et al. .................... 422/56 |
| 4,017,261 | 4/1977 | Svoboda et al. .................... 422/56 |
| 4,098,575 | 7/1978 | Matsushito . |
| 4,252,903 | 2/1981 | Kallies .................... 422/56 X |
| 4,275,031 | 6/1981 | Fischer et al. .................... 436/166 X |
| 4,387,164 | 6/1983 | Hevey et al. .................... 422/56 X |

Primary Examiner—Arnold Turk
Attorney, Agent, or Firm—Donald M. Sell; James A. Smith; Richard Francis

[57] ABSTRACT

An article for testing liquid for free fatty acid comprises a substantially nonreactive, neutral and non-buffering, porous, absorbant support material having at least one portion thereof which contains a composition comprising an effective amount of acid-base indicator capable of changing color, when the predetermined amount of base has reacted with the known amount of free fatty acid, in a pH range on the order of 6–10, a predetermined amount of base compound reactive with free fatty acid and being present in an amount equivalent to a known concentration of free fatty acid, and about 30–99.5 parts by weight of non-volatile material of a substantially colorless, substantially neutral, humectant polyalkylene glycol organic solvent which is substantially non-volatile under ambient conditions. An organic liquid to be tested is contacted with the article and any color change in the article after the passage of sufficient time is observed.

8 Claims, 6 Drawing Figures

TEST METHOD AND ARTICLE FOR ESTIMATING THE CONCENTRATION OF FREE ACID IN LIQUID

CROSS REFERENCE TO RELATED APPLICATION

This is a continuation-in-part of copending application Ser. No. 554,184, filed Nov. 22, 1983, now abandoned, which application is a continuation-in-part of application Ser. No. 218,356, filed Dec. 19, 1980, now abandoned.

TECHNICAL FIELD

This invention relates to a method and test strip for use in estimating the free acid content in liquids such as cooking oil.

BACKGROUND ART

Great quantities of cooking oil and fats are utilized daily by cooks and food processors to prepare food. Typical cooking methods involve immersing the food to be cooked, e.g., in a wire basket, into a heated vat of cooking oil and permitting the food to remain therein until cooked. Cooking under such circumstances gives the food its own distinctive cooked flavor.

Unfortunately, as cooking oils and fats are used, there is a progressive build up of undesirable constituents such as free fatty acids. Cooking oils and fats used for frying foods are generally composed of triglycerides with minor amounts of free fatty acids. The chemical breakdown of the triglycerides, mainly caused by hydrolysis and oxidation, forms fatty acids, short chain compounds such as aldehydes, ketones and acids. If degradation proceeds to any significant extent, the degradation products impart an unacceptable flavor to the cooked foods.

As the concentration of free fatty acid builds, the cooking oil progressively assumes undesirable characteristics such as foaming, darkening, smoking, forming gums and residues and imparting distinctive interfering flavors to the food being cooked.

Some cooks and food processors merely add new cooking oil or fat to the degraded material to extend the useful life of the cooking oil. While this is temporarily effective, the problem will be repeated as additional degradation takes place. Other cooks merely discard the entire batch of cooking oil or fat and replace it with a fresh supply. Many cooks and some food processors discard their cooking oil after a scheduled use time to preserve the integrity of the flavor of their cooked food notwithstanding the fact that degradation may not have occurred to an extent to even remotely interfere with the food. The latter method causes considerable waste and the unnecessary expenditure of considerable man hours, if the cooking oil or fat is discarded prematurely.

Various methods have been devised to quantitatively or qualitatively determine the degree of degradation and/or fatty acid content, but these generally have one or more problems associated therewith. One method involves frequently monitoring the taste of the food and, when the food begins to assume an off taste, utilize that as a point at which the oil is replaced or rejuvenated. Since this method requires frequent testing the flavor of the food may vary. This method is undesirably subjective. Other methods include monitoring the color of the oil, since it darkens with degradation, either by visually observing it or by using photoelectric devices to make the observation. These methods are undesirable because they generally require the removal and handling of small volumes of hot oil. Additionally, the photoelectric examination requires relatively expensive equipment which must be maintained and is subject to failure. Another method involves titrating small samples of the oil with a standard basic solution. The titration method is undesirable because it also requires removing samples of typically hot oil and also requires the preparation of standard titration solutions and the maintenance of certain laboratory equipment for use therewith, typically not found in most restaurants and some food processing facilities. Some test methods have been devised utilizing test papers, but they have generally been unacceptable because they have not been sufficiently accurate, are difficult to use, or give misleading results.

Illustrative of the prior art dealing with testing oils, fats and the like for degradation, fatty acid content, or similar purposes are the following U.S. Patents:

Bergstrom et al U.S. Pat. No. (2,770,530), Seeman et al U.S. Pat. No. (3,030,190), Apter U.S. Pat. No. (3,615,226) and Elliott et al U.S. Pat. No. (2,953,439) disclose various "wet" methods of testing oils which require the removal of small amounts of oil from the main batch. Eiseman U.S. Pat. No. (3,238,020) discloses an oil test strip containing an indicator and an aliphatic polyhydroxy compound. Davis U.S. Pat. No. (3,420,635) discloses a fruit ripeness telltale formed of a sheet of plastic having thereon a color-changing composition including an acid-base indicator and a solid absorbent for $CO_2$ such as calcium hydroxide to detect when the fruit is ripened and a small amount of hydroscopic material such as calcium hydroxide to detect when the fruit is ripened and a small amount of hydroscopic material such as calcium chloride to insure the presence of moisture. Pickup et al U.S. Pat. No. (3,580,704) disclose the colorimetric indicators for determining pH of motor oil with paper treated with an acid-indicator and a non-aqueous, non-volatile liquid solvent in which the oil and indicator are soluble. Matsushits U.S. Pat. No. (4,098,575) discloses a test paper impregnated with potassium iodide to determine the peroxide value of oils in fats.

SUMMARY OF THE INVENTION

The present invention provides an article for quantitatively estimating the acid content (including free fatty acid) in organic liquids such as cooking oils, motor oil and the like. The article of the invention rapidly (i.e., in 10 minutes or less) quantitatively estimates the total acid content in liquid. The article is preferably in the form of a strip which can easily be submersed in the cooking oil and removed with a predetermined volume of oil imbibed thereon. Removal of test samples of the oil is not otherwise required, thereby avoiding liquid handling steps. The article of the invention provides a rapid, convenient means of determining the free fatty acid content in cooking oil, providing results in less than an hour, preferably less than one minute.

The article of the present invention comprises a substantially nonreactive, neutral and nonbuffering, porous, oil-absorbent support material having at least one test area capable of absorbing a predetermined volume of the liquid being tested. Each test area contains a predetermined amount of base compound reactive with free fatty acid and being present in an amount equivalent to a known amount of free fatty acid, an indicator capable of changing color, when the predetermined amount of base has reacted with the known amount of free fatty acid, in a pH range on the order of 6-10, and about 30-99.5 parts by weight (based upon the weight of the non-volatile constituents of the solvent, indicator and the base compound) of a substantially colorless, substantially neutral, humectant polyalkylene glycol organic solvent which has a molecular weight of less than about 2,000 and is substantially non-volatile under ambient conditions.

A preferred article of the invention includes spacially separated test areas, each of which contain the composition, but with varying amounts of base compound in each to provide the capability of identifying a range of amounts of free fatty acid in the organic liquid. The method of the invention comprises absorbing a known volume of the liquid to be tested in the test area of a test article described above and observing any color change in the article after the passage of sufficient time.

DRAWING

The invention may be further understood by reference to the drawing, wherein

DESCRIPTION OF THE PREFERRED EMBODIMENTS

Figure 1:
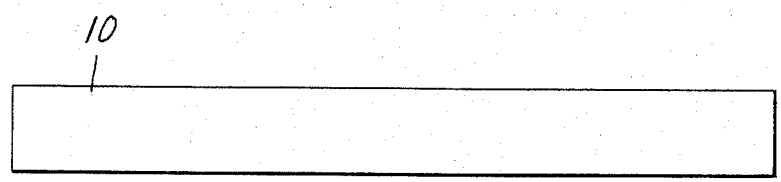
FIG. 1 is a top plan of an embodiment of the article of the invention.
Figure 2:
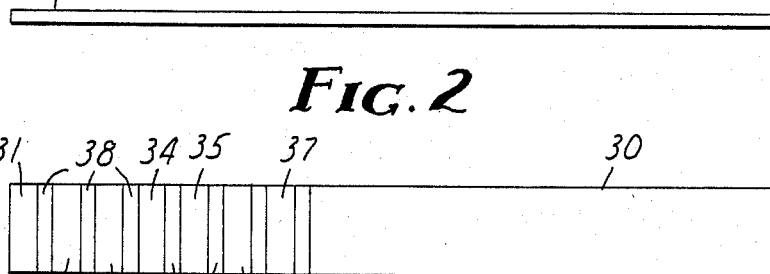
FIG. 2 is a side view of the article of FIG. 1.

Referring now to FIGS. 1-2, there is shown an article in the form of a strip 10 for estimating the free fatty acid content in organic liquids such as cooking oil. Strip 10 is formed of a substantially nonreactive, neutral and non-buffering, oil-absorbent support material which may be a woven or a nonwoven material. The preferred porous support material is formed of porous paper such as filter paper (e.g., Whatman's #1 filter paper). Other useful support materials include nonwoven glass filter material, open-celled foam and woven fabrics such as woven cotton cloth. The support material absorbs a controlled volume of oil in a given reasonable period of time, typically less than 1 minute, preferably less than 5 seconds. While the support material preferably is in the form of an elongate strip, it may also have other forms, e.g., a tube, disc, rod or the like.

Each test area of the support material contains a predetermined amount of base compound reactive with free fatty acid and being present in an amount equivalent to a known amount of free fatty acid an indicator capable of changing color, when the predetermined amount of base has reacted with a known amount of free fatty acid, and about 30-99.5% by weight (based upon the weight of the non-volatile constituents) of a substantially colorless, substantially neutral, humectant organic solvent which is substantially non-volatile under ambient conditions.

The article of FIGS. 1-2 will be capable of changing color after a particular fatty acid content has been achieved in the organic liquid being tested and present in the support material. The amount of fatty acid at which the color change takes place is determined by the amount of base compound in the article. The amount of base should be adjusted to correlate to the desired concentration of free fatty acid. That is, if the amount of base is selected to provide a color change at 1% fatty acid, a color change will take place at 1% and higher concentrations of free fatty acid.

Figure 3:
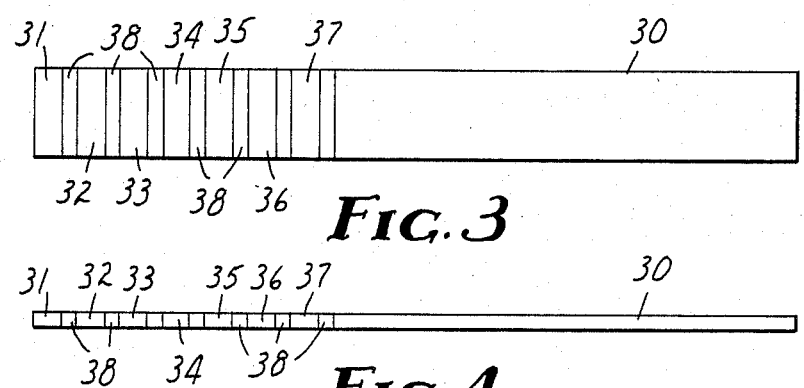
FIG. 3 is a top plan view of another embodiment of the article of the invention having the capability of determining the fatty acid content over a range of concentrations.
Figure 4:
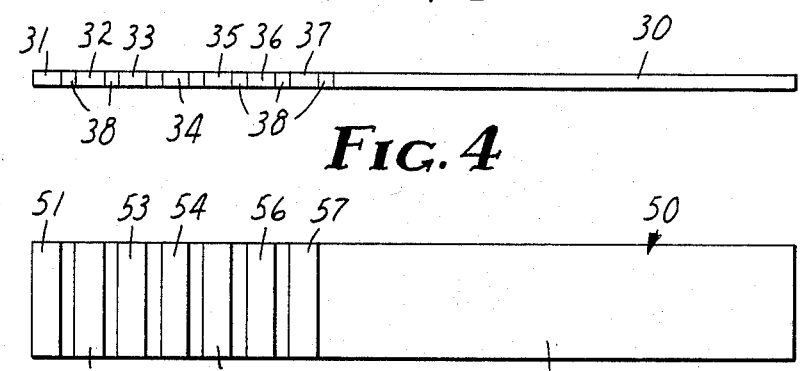
FIG. 4 is a side view of the article of FIG. 3.
Figure 5:
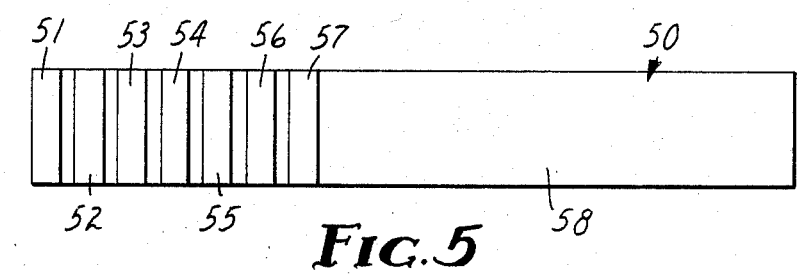
FIG. 5 is a top plan view of yet another embodiment of the article of the invention having a similar capability as the article of FIGS. 3-4.
Figure 6:
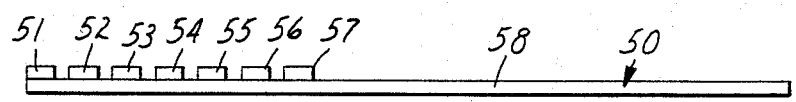
FIG. 6 is a side view of the article of FIG. 5.

The preferred article according to the present invention has the capability of revealing a range of free fatty acid content, for example, in increments of 1% from 0 to 10%. Such articles are shown in FIGS. 3-6. Referring to FIGS. 3-4, there is shown an article in the form of strip 30 having test areas 31, 32, 33, 34, 35, 36 and 37, each containing the impregnant composition described above, except having varying amounts of base compound to reflect a varying range of free fatty acid content. The test areas are separated by a barrier stripe 38 which prevents migration of impregnant composition liquids from the test area. FIGS. 5-6 show yet another embodiment of the article of the invention in the form of strip 50 bearing test area segments 51-57, each containing varying amounts of base material to reflect a range of fatty acid content. The area segments are bits of support material which are impregnated as described above and adhered to a carrier strip 58. Other modifications of the article according to the present invention may be made without departing from the scope of the claims.

The support material may be formed of any substantially unreactive, i.e., pH neutral, nonbuffering, and chemically non-reactive porous, oil-absorbent woven, nonwoven, or the like material which has the capability of holding and retaining a sufficient amount of the active ingredients which will be contained therein. The support material is preferably light colored or colorless. Suitable support materials may be formed of porous paper such as filter paper, preferably Whatman's #1 filter paper, non-woven glass filters, open-celled foams, webs of polymeric microfibers, and woven cotton cloth.

The impregnant solution which is contained in the support material is formed of humectant solvent, indicator and base compound. The humectant solvent is a substantially non-volatile, substantially colorless, substantially neutral liquid that is soluble in water and capable of solubilizing the indicator and preferably the base compound. Suitable humectant solvents include dihydroxy aliphatic polyethylene glycol compounds such as available from the Union Carbide Company under the trade designation "Carbowax" 200, "Carbowax" 400 and "Carbowax" 600, and "Carbowax" 1500. The number appearing after the tradename refers to the molecular weight of the glycol. The humectant solvent comprises about 30-99.5% of the non-volatile content of the impregnant composition.

The base compound may be any organic or inorganic base compound with sufficient reactivity to react with the fatty acids and inorganic acids. Some examples of useful base compounds include sodium carbonate, sodium bicarbonate, potassium carbonate, potassium bicarbonate, tetramethyl guanidine, guanidine carbonate and amino silane (available under the trade designation "A-1100" silane from the Union Carbide Company). The amount of base compound may vary from 0.4% to 75% based upon the non-volatile constituents of the impregnant composition. The amount of base compound is controlled, depending upon the amount of oil imbibed upon the support, to provide in the article an amount which permits quantification of the amount of acid being measured.

The acid-base indicator may be any organic acid-base indicator dye or combination thereof which is capable of providing a color change, preferably a very distinct color change, when base compound has reacted with the fatty acids and inorganic acids, in the pH range of 6-10. Suitable indicators include m-cresol purple, neutral red, Thymol blue, phenol red and cresol red.

For strips which are capable of revealing a range of acid concentrations of the type shown in FIGS. 3-4, a continuous stripe of barrier material is utilized to define test areas to prevent migration of the ingredients from one test area to another. The barrier material is any suitable material for providing this function. Examples of suitable barrier materials include polysiloxanes, polyacrylates and methacrylates, epoxy resins and the like. Additionally, the barrier may be provided by the construction shown in FIGS. 5-6 by employing a barrier type backing film 58 upon which the test area segments are adhered. Such backing materials may be formed of thermoplastic sheet material such as polyethylene, polypropylene or the like.

The simplest form of the article of the invention may be prepared by mixing the humectant solvent, base compound, indicator and additional volatile solvent such as water or organic solvent, if required, to provide a solution, and impregnating the support material with the solution to provide the desired composition within the base material and permitting the support material to dry.

Articles of the type depicted in FIGS. 3-4 may be prepared by applying parallel separate stripes of barrier material to the base material and impregnating the areas defined between the stripes with impregnant compositions having varying amounts of base compound. The barrier stripes should be applied in a sufficient width to prevent migration between areas. Typical barrier widths are on the order of 1 to 10 mm. Segments of support material, each having or subsequently being provided with varying amounts of base compound in the impregnant composition may be adhered to a barrier substrate by suitable adhesive or by heat lamination to provide the article depicted in FIGS. 5-6. If the segments are to be heat laminated, it is preferred to impregnate the segments after lamination to avoid any heat induced alteration in their components. Additionally, an article according to the invention may be prepared by mixing the impregnant materials with paper or web-forming fibers and casting the web or paper from this mixture by conventional techniques. Other ways of producing the article of the invention will become apparent to those skilled in the art, once apprised of the present disclosure.

EXAMPLES

The invention is further illustrated by the following examples, wherein all parts are by weight, unless otherwise specified.

EXAMPLE 1

A 110 mm diameter disc of Whatman's #1 filter paper was treated by spraying with a solution consisting of

| Ingredient | Parts |
| --- | --- |
| m-cresol purple indicator | 0.04 |
| ethylene glycol humectant non-volatile solvent available under the trade designation "Carbowax" 200 | 30.0 |
| sodium bicarbonate base compound | 0.78 |
| water | 69.18 |

The paper was coated to provide a wet coating weight of 15 mg per cm$^2$ and thereafter dried at room temperature to a constant weight of 3 mg per cm$^2$. A strip of the treated paper was dipped into oil containing known quantities of free fatty acid. The strip changed from blue to yellow in less than one hour after being dipped in oil containing free fatty acid to provide a concentration using an acid number in excess of 5. No color change was noted in the oil containing acid to provide an acid number less than 5.

EXAMPLE 2

An article according to the present invention was prepared by laminating a 2 cm square piece of Whatman's #1 filter paper over the 2 cm square end portion of the polyethylene side of a 2 cm × 10 cm strip of laminate film consisting of a layer of polyethylene adhered to a layer of polyester and available under the trade designation "Scotchpack" heat sealable polyester film. Lamination of the paper to the film was accomplished with a "Robot" heat sealer (Model RTP-F, available from Pack-Rite machines) by heating the juxtaposed paper film assembly therein between jaws heated at 150° C., holding the assembly therein for 8 seconds at a jaw pressure of 0.25 kg per cm$^2$, to cause the paper to adhere to the polyethylene surface. The paper was then treated with the solution described in Example 1 to provide a wet coating weight of 15 mg per cm$^2$ and dried at room temperature to a constant weight to provide a dry coating weight of 3 mg per cm$^2$. The resultant strip performed substantially the same as the strip described in Example 1.

EXAMPLE 3

An article of the type depicted in FIGS. 5 and 6 according to the present invention having multiple test areas corresponding to acid numbers of 1, 3, 5 and 7 was produced by laminating four 0.5 cm by 1 cm pieces of Whatman's #1 filter paper on the polyethylene side of a 1 cm × 10 cm strip of the polyethylene:polyester laminate film described in Example 2 with the four strips of paper being separated by 0.5 cm and being parallel on their 1 cm sides with their 0.5 cm sides aligned along the 10 cm sides of the laminate. The assembly was laminated in the heat sealer described in Example 2 at 150° C. for 10 seconds at a pressure of 0.24 kg per cm$^2$. The four segments of filter paper were treated respectively with the following solutions:

| Ingredient<br>Acid No. | Parts<br>1 | Parts<br>3 | Parts<br>5 | Parts<br>7 |
| --- | --- | --- | --- | --- |
| m-cresol purple indicator | 0.04 | 0.04 | 0.04 | 0.04 |
| ethylene glycol humectant solvent available under the trade designation "Carbowax" 200 | 30.0 | 30.0 | 30.0 | 30.0 |

-continued

| Ingredient | Parts 1 | Parts 3 | Parts 5 | Parts 7 |
|---|---|---|---|---|
| Acid No. | | | | |
| sodium bicarbonate base compound | 0.275 | 0.5 | 0.78 | 1.07 |
| water | 69.69 | 69.46 | 69.18 | 68.88 |

Each of the coating weights was approximately 15 mg per cm$^2$ wet, drying to a constant 3 mg per cm$^2$ weight at room temperature. The resultant dried strip was dipped into a test oil sample containing fatty acid concentration of less than acid number one. No color change in the strip was observed, i.e., all of the zones remained blue. A second strip was dipped into oil containing fatty acid to provide an acid number greater than 1 but less than 3. A color change from blue to yellow in the test area treated to correspond to an acid number of 1 was observed, but no color change in the remaining treated test areas indicating acid numbers of 3 or more were noted. The remaining test areas were found to perform in a similar manner when the free fatty acid concentration was increased.

EXAMPLE 4

A preferred article depicted in FIGS. 3-4 of the drawing according to the present invention having the capability of detecting the range of fatty acid concentrations corresponding to acids number 1, 3, 5 and 7 was prepared. A 1 cm×10 cm strip of Whatman's #1 filter paper was provided with barrier stripes consisting of a two part silicone resin available from the Dow Corning Company as "Dielectric Gel" and applied by utilizing a 1 cc hypodermic syringe fitted with a 25 gauge needle to provide parallel stripes on the strip of filter paper parellel to the 1 cm ends 2 mm wide and separated by approximately 4 mm to provide four 4 mm×10 mm zones of untreated paper. Each zone was treated, respectively, with the four impregnant compositions described in the previous example to provide test areas having respectively the capability of detecting acid numbers 1, 3, 5 and 7. The test strip performed substantially the same as described in Example 3.

EXAMPLES 5 and 6

Test strips, respectively identified below as Examples 5 and 6, were prepared respectively using "Whatman" No. 1 and No. 3 mm "Chrom" filter papers as support materials. These support materials were coated in stripes as described in Example 3. The amount of each ingredient impregnated in each stripe was controlled to give the amount of base compound shown in the Table below.

A soybean shortening, available from Hunt-Wesson, Incorporated under the tradename "Crystal", was heated to 150° C. The color indicating zones of a test strip were saturated with the hot shortening and lightly blotted with an absorbant material to remove excess shortening. The strip was weighed before and after saturation and the oil absorption in each zone calculated.

Test shortening samples containing known quantities of fatty acid were made by mixing the soybean shortening with predetermined amounts of oleic acid to produce samples respectively containing 3.5% by weight (acid number 7.0) or 1.5% by weight (acid number 3.0) oleic acid. Examples 5 and 6 test strip were immersed in each of the test shortening samples and the test zones changing color were observed and are reported in Table I.

TABLE I

| | Example 5 | Example 6 |
|---|---|---|
| Support material | Whatman No. 1 | Whatman 3 mm Chrom |
| Uncoated basis weight | 87 g/m$^2$ | 185 g/m$^2$ |
| Uncoated thickness | 0.18 mm | 0.33 mm |
| Oil absorption, per zone | 4 mg | 11.5 mg |
| Zone area, average | 60 mm$^2$ | 55 mm$^2$ |
| Amount of base Compound Moles NaHCO$_3$ per zone | | |
| Zone A | 2.7 × 10$^{-7}$ | 5 × 10$^{-7}$ |
| Zone B | 5.0 × 10$^{-7}$ | 8 × 10$^{-7}$ |
| Zone C | 7.6 × 10$^{-7}$ | 13 × 10$^{-7}$ |
| Zone D | 10.7 × 10$^{-7}$ | 18 × 10$^{-7}$ |
| test shortening % oelic acid | 3.5% | 1.5% |
| Test shortening equivalent acid number | 7 | 3 |
| Moles oleic acid absorbed per zone | 5.0 × 10$^{-7}$ | 6.0 × 10$^{-7}$ |
| Zones changing color | A and B | A |
| Zones not changing color | C and D | B, C and D |

As can be seen, each test article correctly identified the fatty acid content in the test shortening.

To show the effectiveness of polyethylene glycol humectant solvents having a molecular weight of less than about 2000 in obtaining a rapid color change in the test strip and method of the present invention, several humectant solvents were evaluated in test strips substantially as described in Example 1 except substituting for the humectant solvent, the solvent shown in Table II below.

TABLE II

| Humectant Solvent | | Time for |
|---|---|---|
| Generic Name | Tradename | Change |
| None | None | >4 hours |
| polyethylene glycol MW200 | "Carbowax" 200 | 15-90 sec. |
| polyethylene glycol MW600 | "Carbowax" 600 | 15-90 sec. |
| polyethylene glycol MW1500 | "Carbowax" 1500 | 2-3 min. |
| diethylene glycol ethyl ether | — | >1 hour |
| dipropylene glycol methyl ether | — | >1 hour |
| 2-methoxy ethanol | — | >1 hour |
| 2-(2-methoxy ethoxy) ethanol | — | >1 hour |
| 1-methyl-2-pyrolidinone | — | >1 hour |
| alkylphenoxy polyethoxy ethanol | "Triton" X-100 | >1 hour |
| glycerine | — | >1 hour |
| ethylene glycol | — | >1 hour |
| polyethylene glycol MW4000 | "Carbowax" 4000 | >4 hours |
| Condensate of ethylene oxide with a hydrophobic base formed by condensing propylene oxide and propylene glycol | "Pluronic" L-42 | >24 hours |
| Polyethylene glycol ether of linear alcohol | "Tergitol" 15-S-9 | >24 hours |
| dimethyl sulfoxide | — | no change |

The polyethylene glycols having a molecular weight of 1500 or less are the only humectant solvents shown in the table which provide for rapid color change.

We claim:

1. An article for determining the concentration of free fatty acid in a liquid such as cooking oil, motor oil, and the like, said article comprising a substantially non-reactive, neutral, porous and oil absorbent, support material having at least one defined test area capable of absorbing a known volume of said liquid, said test area being impregnated with
- (a) a predetermined amount of base compound reactive with acid absorbed in said test area of said support and being present in said test area in an amount equivalent to a known amount of free fatty acid;
- (b) an effective amount of acid-base indicator capable of changing color, when the predetermined amount of base has reacted with the known amount of free fatty acid, in a pH range on the order of 6–10; and
- (c) about 30–99.5 parts by weight based upon the total weight of the non-volatile constituents of (a), (b) and (c) of a substantially colorless, substantially neutral, humectant dihydroxy aliphatic polyethylene glycol organic solvent which has a molecular weight less than about 2000 and is substantially non-volatile under ambient conditions.

2. The article of claim 1 wherein said support material is formed of paper.

3. The article of claim 1 wherein said base compound is selected from the group consisting of sodium carbonate, sodium bicarbonate, potassium carbonate, potassium bicarbonate, tetramethyl guanidine, guanidine carbonate and amino silane.

4. The article of claim 1 wherein said indicator is selected from the group consisting of m-cresol purple, neutral red, Thymol blue, phenol red and cresol red.

5. The article of claim 1 wherein said support material has a plurality of test areas, each containing said composition but with varying predetermined amounts of said base compound in each of said test areas to provide amounts equivalent to a range of known amounts of free fatty acid.

6. The article of claim 5 wherein said test areas are separated by barrier stripes which prevent the migration of ingredients from one test area to an adjacent test area.

7. The article of claim 5 wherein said test areas are spacially separated and adhered to a carrier strip formed of a barrier material which prevents migration of ingredients from one of said test areas to another.

8. A method of determining the concentration of free fatty acid in a liquid comprising
- (a) absorbing a predetermined volume of the liquid to be tested in a test area of a test article comprising a substantially non-reactive, neutral, porous, oil absorbent and nonbuffering support material having at least one test area impregnated with a composition comprising
  - (1) a predetermined amount of base compound reactive with free acid and being present in an amount equivalent to a known amount of free fatty acid absorbed in said test area;
  - (2) an effective amount of acid-base indicator capable of changing color, when the predetermined amount of base has reacted with the known amount of free fatty acid, in a pH range on the order of 6–10;
  - (3) about 30–99.5 parts by weight based upon the non-volatile constituents of the total weight of (1), (2) and (3) of a substantially colorless, substantially neutral, humectant dihydroxy aliphatic polyethylene glyco organic solvent which has a molecular weight less than about 2000 and is substantially non-volatile under ambient conditions; and
- (b) observing any color change in said article.

* * * * *